US008280747B1

(12) United States Patent
Sholtis et al.

(10) Patent No.: US 8,280,747 B1
(45) Date of Patent: Oct. 2, 2012

(54) SYSTEMS AND METHODS FOR HEALTH INFORMATION ANALYSIS AND STORAGE

(75) Inventors: Steven A. Sholtis, El Dorado Hills, CA (US); Terry F. LeClair, Fremont, CA (US)

(73) Assignee: Intuit Inc., Mountain View, CA (US)

( * ) Notice: Subject to any disclaimer, the term of this patent is extended or adjusted under 35 U.S.C. 154(b) by 935 days.

(21) Appl. No.: 11/741,564

(22) Filed: Apr. 27, 2007

(51) Int. Cl.
*G06Q 50/00* (2006.01)
(52) U.S. Cl. .......................................................... 705/2
(58) Field of Classification Search .................. 705/2, 3
See application file for complete search history.

(56) References Cited

U.S. PATENT DOCUMENTS

| 7,523,505 B2 * | 4/2009 | Menschik et al. | 726/26 |
| 7,529,685 B2 * | 5/2009 | Davies et al. | 705/3 |
| 2002/0128871 A1 * | 9/2002 | Adamson et al. | 705/3 |
| 2004/0260577 A1 * | 12/2004 | Dahlin et al. | 705/2 |

OTHER PUBLICATIONS

"OR-2005 PricePoint System" http://web.archive.org/web/20060426203833/http://www.orpricepoint.org/, web archive dated Apr. 26, 2006 (orpricepoint).
"ahd.com: American Hospital Directory"; http://web.archive.org/web/20060422030457/http://www.and.com/sample_outpatient.html, web archive dated Apr. 22, 2006 (ahdcom).
"Encore", http://web.archive.org/web/20061113115857/http://www.encoresyspros.com/data_warehouse_content.htm, web archive dated Nov. 13, 2006 (encore).
"Developing Healthcare Business Intelligence Solutions" http://web.archive.org/web/20070203081838/http://www.dgapartners.com/files/DGA-Healthcare-Business-Intelligence-Solutions.pdf, web archive dated Feb. 3, 2007 (DGA-Healthcare-Business-Intelligence-Solutions).
"HealthGrades", http://web.archive.org/web/20070418193238/http://www.healthgrades.com/, web archive dated Apr. 18, 2007 (healthgrades).

* cited by examiner

*Primary Examiner* — Gerald J. O'Connor
*Assistant Examiner* — Neha Patel
(74) *Attorney, Agent, or Firm* — McKay and Hodgson, LLP; Philip McKay; Sean P. Lewis

(57) ABSTRACT

Systems and methods for a healthcare information collection and analysis system to collect health information, aggregate and/or analyze the information, and use the collected information to provide relevant information in an organized form to one or more system users. The information may be used to provide system users with health information about health conditions and their related procedures and medications. The information may be used by the system users, for example, to determine what procedures and medications they can expect with certain health conditions. The information may also help system users select healthcare providers and may provide system users with a range of approximate costs to expect for the procedures and medications.

14 Claims, 14 Drawing Sheets

Search Result 1 of 3:

Health Condition: Hypertrophic Cardiomyopathy — 403
    Also known as:
        Hypertrophic Obstructive Cardiomyopathy (HOCM)
        Idiopathic Hypertrophic Sub-aortic Stenosis (IHSS)
        Muscular Sub-aortic Stenosis

Diagnosis Procedures: — 405
    Procedure 1 (100%): Electrocardiogram ($350)
    Procedure 2 (75%): Chest X-Ray
    Procedure 3 (75%): Echocardiogram
    Procedure 4 (34%): Cardiac Catheterisation
    Procedure 5 (12%): Cornary Angiography

Treatment Medication: — 407
    Medication 1 (63%): Propranolol
    Medication 2 (42%): Verapamil

Treatment Procedures: — 409
    Procedure 1 (23%): Surgical Myectomy
    Procedure 2 (18%): Pacemaker
    Procedure 3 (12%): Implantable Cardioverter Defibrillator (ICD)
    Procedure 4 (5.1%): Valve Replacement
    Procedure 5 (2.1%): Heart Transplant

| | | |
|---|---|---|
| User 1 (99997 zip code) | User 6 (99998 zip code) | — 411 |
| User 2 (99997 zip code) | User 7 (99999 zip code) | |
| User 3 (99997 zip code) | User 8 (99999 zip code) | |
| User 4 (99998 zip code) | User 9 (99999 zip code) | |
| User 5 (99998 zip code) | More Results... | |

Search Result 1 of 24:

Procedure: Surgical Myectomy
  Health Condition: Hypertrophic Cardiomyopathy —— 503
  User 4 (99998 Zip Code)

Provider: Dr. John Doe (General Heart Associates) —— 505
  Health Plan: Health Plan Family Plus (Health Plan Provider, Inc.) —— 507
  Procedure Initial Cost: $154,000
  Health Plan Approved Cost: $95,000
  User Responsible Amount: $5000 (deductible)

Provider Zip Code: 99997 —— 509
  User Zip Code: 99998 —— 511
  Procedure Date and Time: Jan 12, 2006, 10 AM (Central) —— 513
  Quality Rating of Procedure (provided by User): 8.3 (out of 10) —— 515

Prescribed Medications: Propranolol —— 517
  Medication Cost (1 month): $250 (covered by health plan) —— 519

User 4 (99998 Zip Code)

Health Condition: Hypertrophic Cardiomyopathy — 603

Diagnosis Procedures: — 605
    Procedure 1: Electrocardiogram
    Procedure 2: Chest X-Ray
    Procedure 3: Echocardiogram

Treatment Medication:
    Medication 1: Propranolol — 607

Treatment Procedures:
    Procedure 1: Surgical Myectomy — 609

User 4 (99998 Zip Code)
  Health Plan: Health Plan Family Plus (Health Plan Provider, Inc.)

Health Condition: Hypertrophic Cardiomyopathy
  Provider: Dr. Jane Heart (General Heart Associates, Inc.)

Diagnosis Procedures: ⎯ 705
  Procedure 1: Electrocardiogram
    711 ⎯ Provider: Dr. Jane Heart (Hospital Associates, Inc.)
    713 ⎯ Procedure Initial Cost: $500
    715 ⎯ Health Plan Approved Cost: $350
    717 ⎯ User Responsible Amount: $100 (deductible)

Procedure 2: Chest X-Ray
    Provider: Dr. Jane Heart (Hospital Associates, Inc.)
    Procedure Initial Cost: $425
    Health Plan Approved Cost: $300
    User Responsible Amount: $0 (covered in Proc. 1 deductible)

Procedure 3: Echocardiogram
    Provider: Dr. Tom Gram (Hospital Associates, Inc.)
    Procedure Initial Cost: $950
    Health Plan Approved Cost: $700
    User Responsible Amount: $100 (deductible)

Treatment Medication: ⎯ 707
  Medication 1: Propranolol
    Provider: Dr. John Doe (General Heart Associates, Inc.)
    Medication Initial Cost: $350
    Health Plan Approved Cost: $250
    User Responsible Amount: $0 (yearly deductible met)

Treatment Procedures:
  Procedure 1: Surgical Myectomy ⎯ 709
    Provider: Dr. John Doe (General Heart Associates, Inc.)
    Procedure Initial Cost: $154,000
    Health Plan Approved Cost: $95,000
    User Responsible Amount: $1800 (rest of yearly deductible)

Health Conditions — 905
Procedures — 903
Medications
901

| Health Condition | Symptom | Procedure | Medication | Skip |

— 907

Do you know the name of the health condition? — 911

If you do not know the name of the health condition, we can search for relevant health conditions according to symptoms, procedures, and medications. You can also skip the health condition determination, for example, if you want to search for a specific procedure or medication only.

Do you know the name of the health condition?

< Back      Yes   No

Health Conditions
Procedures
Medications

| Health Condition | Symptom | Procedure | Medication | Skip |

— 907

Please enter the health condition:

[                    ] — 915

< Back      OK

| Health Conditions | Procedures | Medications | |
|---|---|---|---|
| Procedure Name | Provider | Cost | Zip Code | Skip |

Do you want to search by procedure?

If you know the procedure name you are interested in, we can search the database according to procedure name.

Do you want to search by procedure name?

< Back    Yes    No

| Health Conditions | Procedures | Medications | |
|---|---|---|---|
| Procedure Name | Provider | Cost | Zip Code | |

Please enter the procedure name:

⎿ 917

< Back    OK

*FIG. 9d*

SYSTEMS AND METHODS FOR HEALTH INFORMATION ANALYSIS AND STORAGE

BACKGROUND

Individuals receiving a diagnosis may not know what procedures and medications to expect over the course of their treatment. They may also not know the approximate costs of these procedures and medications. Therefore, an individual receiving a new diagnosis may be uncertain as to what they can expect both from a health and financial standpoint.

In addition, health care providers may not advertise the costs of their services (e.g., the cost of a visit or procedure). This may make it difficult for individuals, for example, who do not have insurance and therefore have to look for the most cost effective treatment option. Insurance companies may have the benefit of being able to negotiate a large number of visits and procedures (for a large number of patients) with physicians who may offer a reduced rate for the increased volume (this may be similar for pharmacies and medications, etc.). However, without the benefit of knowing the negotiated rates being offered by some physicians, uninsured individuals may pay the higher initial rates. If individuals knew the reduced rates and/or the rates charged by other physicians, they may be able to negotiate a better rate with their current physician, pharmacy, etc. (or find a more cost effective alternative).

SUMMARY

Various embodiments of a healthcare information collection and analysis system may collect health information from multiple sources, aggregate and analyze the information, and use the collected information to provide information in an organized form to one or more system users. The information may be used to provide system users with health information about health conditions, their related procedures and medications, the costs of the procedures and medications, etc. The information may be used by the system users, for example, to determine what procedures and medications they can expect with certain health conditions. For example, the information may assist system users who receive a diagnosis from their physician determine what they can expect through the course of treating their health condition. The information may also help system users select healthcare providers and may provide system users with a range of approximate costs for the procedures and medications they can expect to encounter.

In some embodiments, information may be collected from various entities including individuals (e.g., healthcare consumers), healthcare providers (e.g., physicians, hospitals, health clinics, etc.), health plan providers (e.g., insurance companies), and other sources. In some embodiments, the information may include types of procedures and medications experienced by individuals (e.g., other system users) with specific health conditions, procedure and medication costs, amount of costs covered by various health insurance plans, and information about the experiences of other healthcare consumers with respect to a specific procedure. Information collected for a procedure may include a date and/or time of the procedure, the healthcare provider of the procedure (e.g., the name of the physician performing the procedure and/or the facility where the procedure was performed), the cost of the procedure, a procedure recipient's health plan and the amount covered by the health plan along with an actual cost to the recipient. In some embodiments, information about a cost the healthcare consumer was able to negotiate from the healthcare provider may also be collected. Collecting other information about the procedures, medications, etc. is also contemplated. For example, the healthcare consumer may provide a quality rating (e.g., a rating that provides a healthcare consumer assessment of the quality of the procedure, follow-up, etc.). Other information may also include medication taken before, during, and after the procedure, the healthcare consumer's zip code, and the zip code of the facility where the procedure was performed. Information may also be collected for other similar procedures (e.g., similar procedures performed on different healthcare consumers by different healthcare providers, etc.).

In some embodiments, various information may be displayed on a results screen as a result of a search (e.g., requested by a system user). In some embodiments, information displayed may include the name of the health condition, diagnosis procedures, treatment medications, treatment procedures, etc. In some embodiments, a percentage of healthcare consumers experiencing the procedure or medication may be provided along with the result. In some embodiments, there may be several results returned. Specific healthcare consumers (e.g., listed with a general descriptor instead of a real name) may also be listed as part of the result. In some embodiments, summary information may be presented for multiple procedures and medications experienced by the healthcare consumer associated with the health condition.

BRIEF DESCRIPTION OF THE DRAWINGS

FIG. 4 illustrates a results screen for displaying the results of a search, according to an embodiment.

FIG. 5 illustrates a procedure specific results screen, according to an embodiment.

FIG. 6 illustrates a result screen with a specific healthcare consumer's experience with a health condition, according to an embodiment.

FIG. 7 illustrates summary information presented for multiple procedures and medications experienced by the healthcare consumer associated with the health condition, according to an embodiment.

FIGS. 9a-d illustrate various embodiments of a heuristic search engine inquiry panels.

Figure 1A:
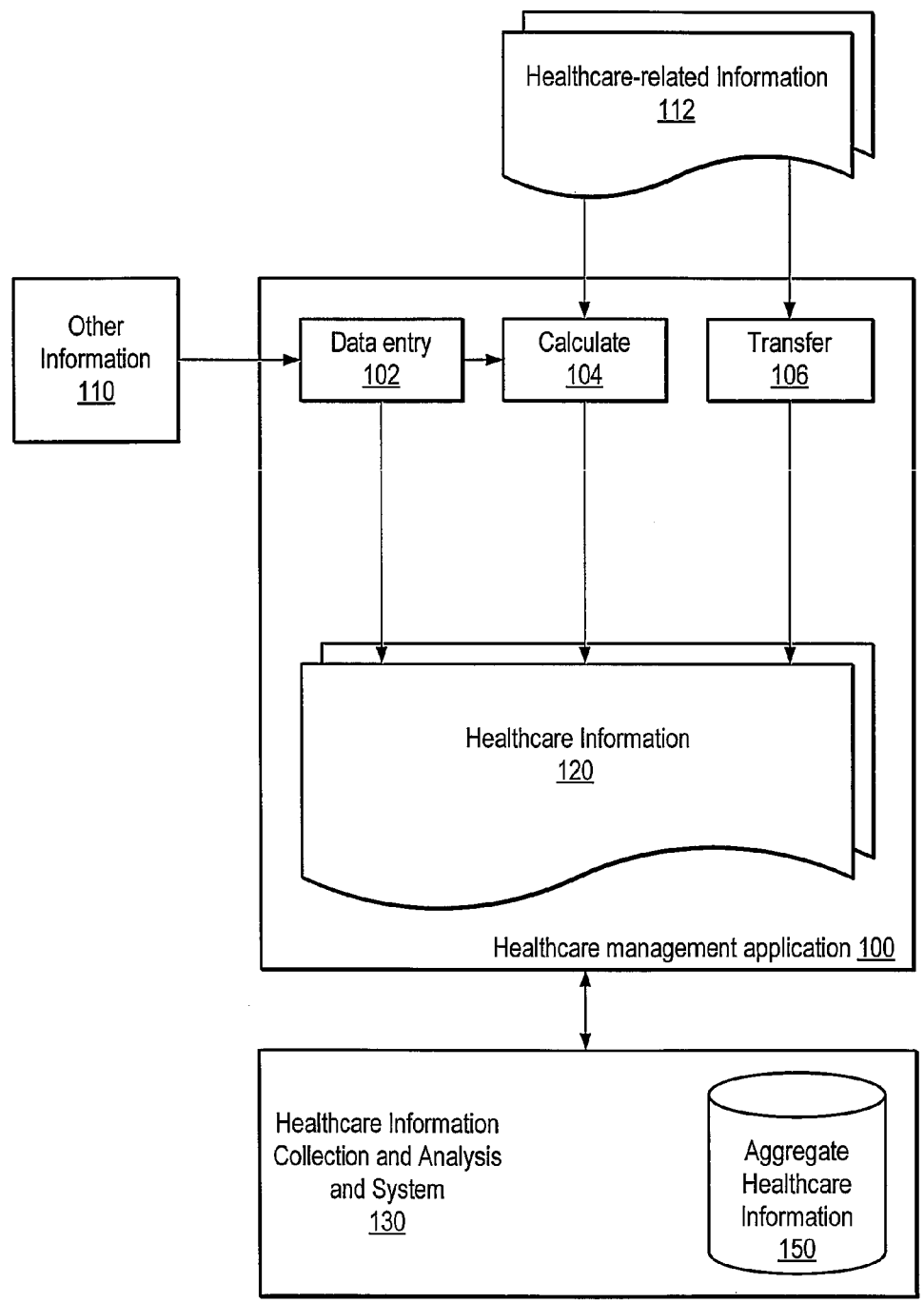
FIGS. 1a-d illustrates a healthcare management application collecting health information, according to an embodiment.

While the invention is described herein by way of example for several embodiments and illustrative drawings, those skilled in the art will recognize that the invention is not limited to the embodiments or drawings described. It should be understood, that the drawings and detailed description thereto are not intended to limit the invention to the particular form disclosed, but on the contrary, the intention is to cover all modifications, equivalents and alternatives falling within the spirit and scope of the present invention as defined by the appended claims. The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including, but not limited to.

DETAILED DESCRIPTION OF EMBODIMENTS

FIGS. 1a-d illustrate a healthcare information collection and analysis system 130, according to an embodiment. Various embodiments of the healthcare information collection and analysis system 130 may collect healthcare information 120 from a plurality of sources (e.g., from health history data streams 241 from various healthcare consumers 202), aggregate and analyze the information, and use the aggregate healthcare information 150 to provide information in an organized form to one or more system users 201. The plurality of sources may include, for example, health plan providers, healthcare providers, and healthcare consumers 202. Other sources are also contemplated. In some embodiments, the healthcare information 120 may be collected from a plurality of source types (e.g., collected from health plan providers and healthcare consumers 202). In some embodiments, the healthcare information collection and analysis system 130 may be implemented through network-based services. As used herein, "system user" includes users of the network-based services used to implement the collection and analysis system 130. The system users may include healthcare consumers 202 who are also sources of the healthcare information 120.

In some embodiments, the aggregate healthcare information 150 may be used to provide system users 201 (e.g., through a search interface) with health information about health conditions 211 and their related procedures 213, medications 215, costs, etc. The information may be used by the system users 201, for example, to determine what procedures 213 and medications 215 they can expect with a given health condition 211 (e.g., related to a recent diagnosis they received). The aggregate healthcare information 150 may also provide system users 201 with information on healthcare providers 203 and ranges of approximate costs to expect. These provided costs may also provide system users 201 with information to help them negotiate with healthcare providers 203 and insurance companies for similar costs and coverages (e.g., with respect to similar procedures 213 and medications 215). In some embodiments, health information for a specific region (e.g., specific to a certain zip code) may be provided to allow system users 201 to view procedures 213 and medications 215 (and, for example, their related costs) in their region. Other uses for the aggregate healthcare information 150 are also contemplated.

In some embodiments, the healthcare information collected for the aggregate healthcare information 150 (used by the healthcare information collection and analysis system 130) may be collected from a healthcare management application 100 used by several system users 201. FIG. 1b illustrates possible sources of healthcare-related information 112 for the healthcare management application 100. In some embodiments, healthcare-related information 112 for the healthcare management application 100 may be entered by individuals (e.g., system users 201 and/or healthcare consumers 202), healthcare providers 203 (e.g., physicians, hospitals, health clinics, etc.), health plan providers 205 (e.g., insurance companies), and other sources 207. In some embodiments, healthcare consumers 202 may include various system users 201 (and vice-versa). Healthcare information may include healthcare-related information 112 collected about health conditions each experienced by a respective plurality of healthcare consumers 202. In some embodiments, some of the healthcare consumers 202 may be included in more than one respective plurality of healthcare consumers 202 (e.g., health consumers who have experienced two or more health conditions). In some embodiments, collecting the healthcare information may include aggregating healthcare information for several respective pluralities of healthcare consumers 202 (corresponding to their respective health conditions) into one database.

In some embodiments, the healthcare-related information 112 may include information about procedures 213 and medications 215 experienced by healthcare consumers 202 during specific health episodes (e.g., related to a specific health condition 211). The aggregate healthcare information 150 may also include healthcare providers 203, health plans, procedure and diagnostic codes, procedure and medication costs, costs covered by various health plans, etc. In some embodiments, more detailed information may be collected with respect to specific procedures 213 and medications 215 experienced by the healthcare consumers 202. Information collected for a procedure 213 may include a date and/or time of the procedure 213, the healthcare provider 203 for the procedure 213 (e.g., the name of the physician performing the procedure 213 and/or the facility where the procedure 213 was performed), the cost of the procedure 213, a procedure recipient's health plan and the amount covered by the health plan along with an actual cost to the recipient, etc. In some embodiments, information about a cost the healthcare consumer 202 was able to negotiate from the healthcare provider 203 may be collected. Other information about the procedure 213 is also contemplated. For example, the healthcare consumer 202 may provide the system a quality rating (e.g., a rating that provides a healthcare consumer's assessment of the quality of the procedure 213, follow-up, etc.). Other information may also include medication 215 taken before, during, and after the procedure 213, the healthcare consumer's zip code, and the zip code of the facility where the procedure 213 was performed. Other geographic segment identifiers may also be used (e.g., area codes). Information may also be collected for similar procedures 213 (e.g., performed on different healthcare consumers 202 by different healthcare providers 203, etc.). Information may also include symptoms (e.g., symptoms experienced by a healthcare consumer 202 with the health condition 211).

Figure 1B:
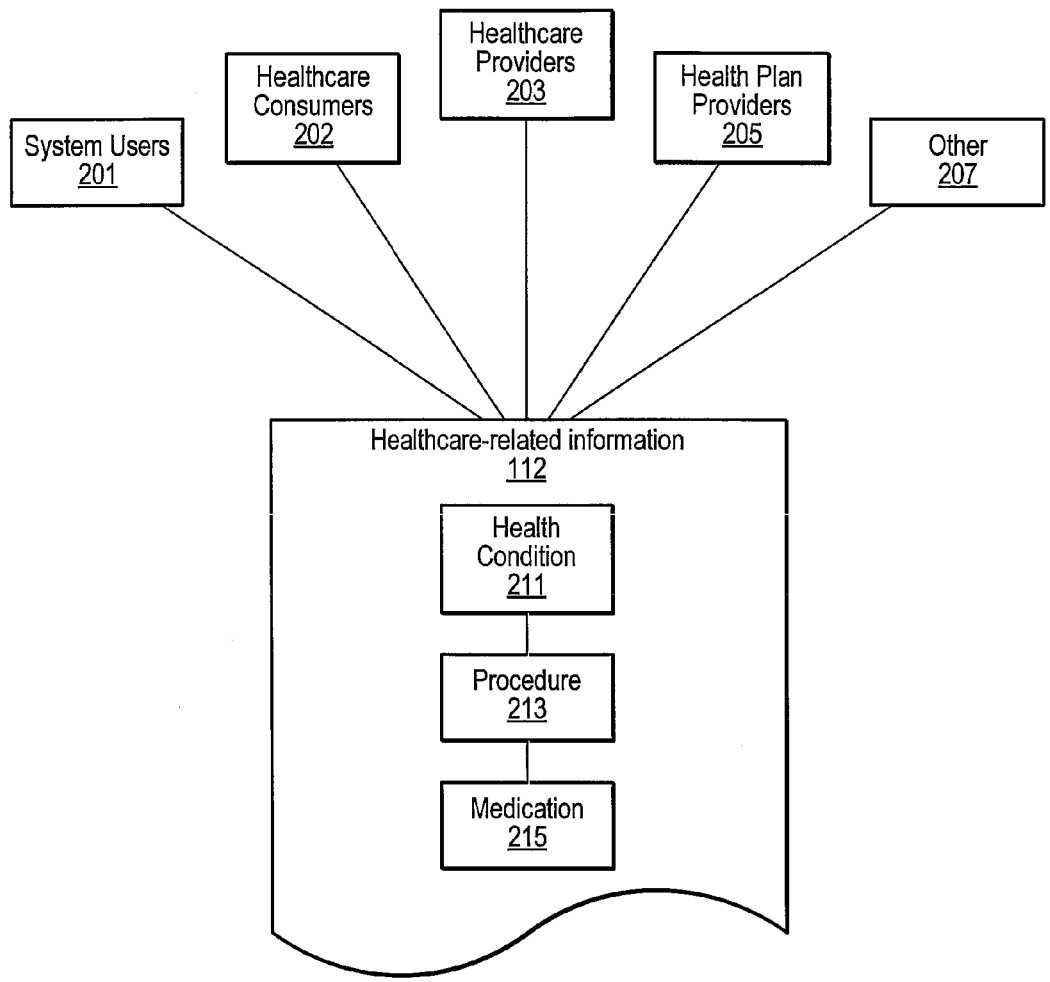
Figure 1C:
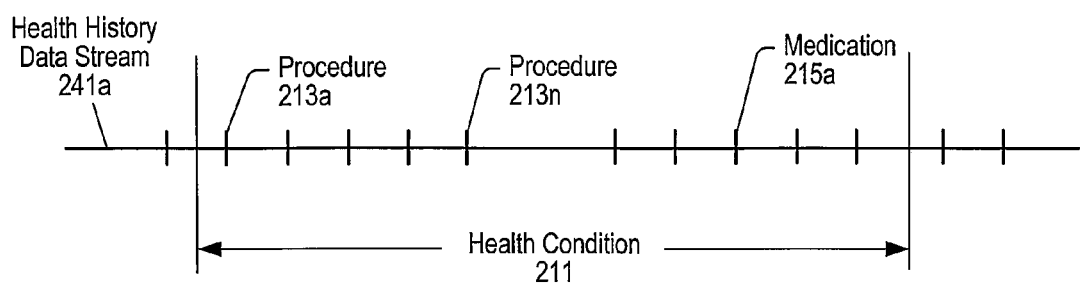

As seen in FIGS. 1a-b, in some embodiments, aggregate healthcare information 150 may be collected from healthcare information 112 provided by healthcare consumers 202 to the healthcare management application 100. The healthcare management application 100 may in some embodiments provide the system user 201 with a framework and tools for collecting, organizing, and managing information related to their health history; past, current and future health services; health insurance plan(s) (e.g., what services are covered, coverage limits, claims status, and explanations of benefits); and finances related to healthcare (e.g., health insurance premiums, deductibles, co-payments, benefit payments, reimbursements from Flexible Spending Accounts (FSAs), Health Reimbursement Accounts (HRAs), health savings accounts, maximum out-of-pocket expenses, and maximum lifetime benefits.) In some embodiments, the healthcare management application 100 may be configured to provide a system user 201 with a comprehensive and detailed health history, or may allow the system user 201 to extract and/or analyze his or her information regarding a particular health condition 211 or event (e.g., an injury or illness) or a particular healthcare-related service (e.g., a particular diagnostic exam or a course of treatment for a chronic condition.)

In some embodiments, the healthcare management application 100 may be implemented as a web-based service to which system users 201 and/or employers may subscribe. In some embodiments, it may be implemented as a stand-alone application, such as one installed and executed on a desktop computer by a system user 201. In some embodiments, a healthcare management application 100 may include both a locally installed application (i.e., a client portion) and a remote, web-based application (i.e., a server portion). For example, in one embodiment, a system user 201 may enter healthcare-related information 112 on a locally installed client application and then may upload the information to a healthcare management service server for secure storage and/or further analysis.

In various embodiments, as seen in FIG. 1b, the healthcare management application 100 may receive information from one or more of: a system user 201 (who may be a healthcare consumer 202), one or more healthcare providers 203, one or more health plan providers 205 (e.g., health insurance representatives), and one or more financial institutions or other sources 207. In some embodiments, the information received and/or managed by the healthcare management application 100 may be formatted according to a standard information exchange format. The healthcare management application 100 may in some embodiments maintain the healthcare-related information 112 in one or more databases (or in other suitable formats) in a local or remote memory, or in a combination of the two. For example, a database located on a healthcare management service server may be configured to securely store healthcare-related information 112 for multiple individual system users 201 or for employees of one or more corporations subscribing to the healthcare management service, while a database stored locally on a system user's computing system may include only his or her own personal health information.

Figure 2:
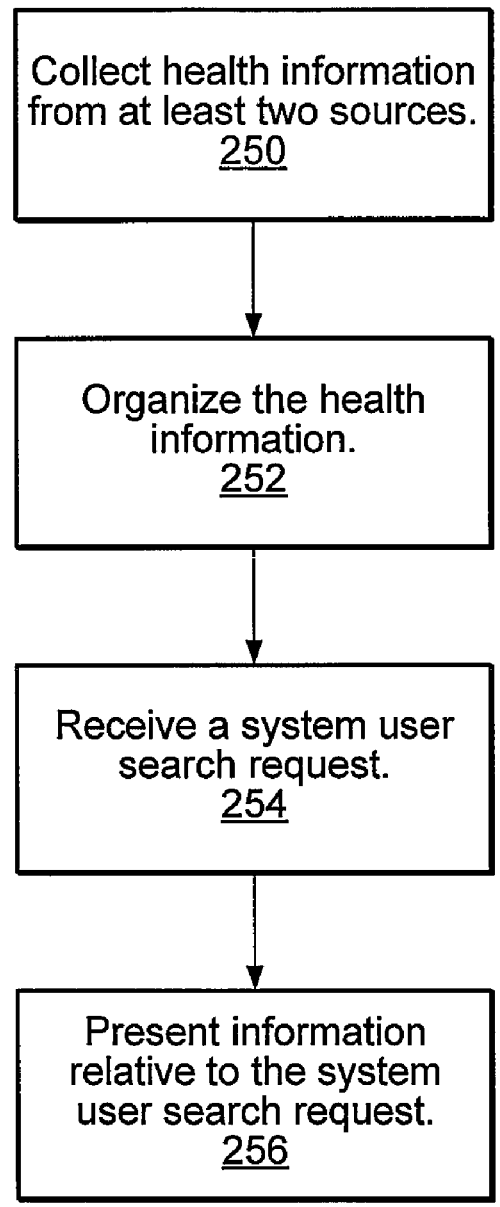
FIG. 2 illustrates a flowchart of a method for collecting and analyzing health information for providing a response to a system user search request, according to an embodiment.

FIG. 2 illustrates a flowchart of an embodiment for collecting and analyzing health information to present to system users 201. It should be noted that in various embodiments of the methods described below, one or more of the elements described may be performed concurrently, in a different order than shown, or may be omitted entirely. Other additional elements may also be performed as desired.

At 250, health information may be collected from at least two sources. Information from the healthcare-related information 112 and/or healthcare information 120 may be collected into aggregate healthcare information 150 used by the healthcare information collection and analysis system 130. For example, in some embodiments, healthcare-related information 112 may be entered into the healthcare management application 100 by two or more healthcare consumers 202, healthcare providers 203, health plan providers 205, or other sources 207. The aggregate healthcare information 150 may include specific information from the healthcare-related information 112 including types of procedures 213 and medications 215 experienced by healthcare consumers 202 with specific health conditions 211 and their healthcare providers 203, health plans, procedure and medication costs, costs covered by their health plans, etc.

Figure 1D:
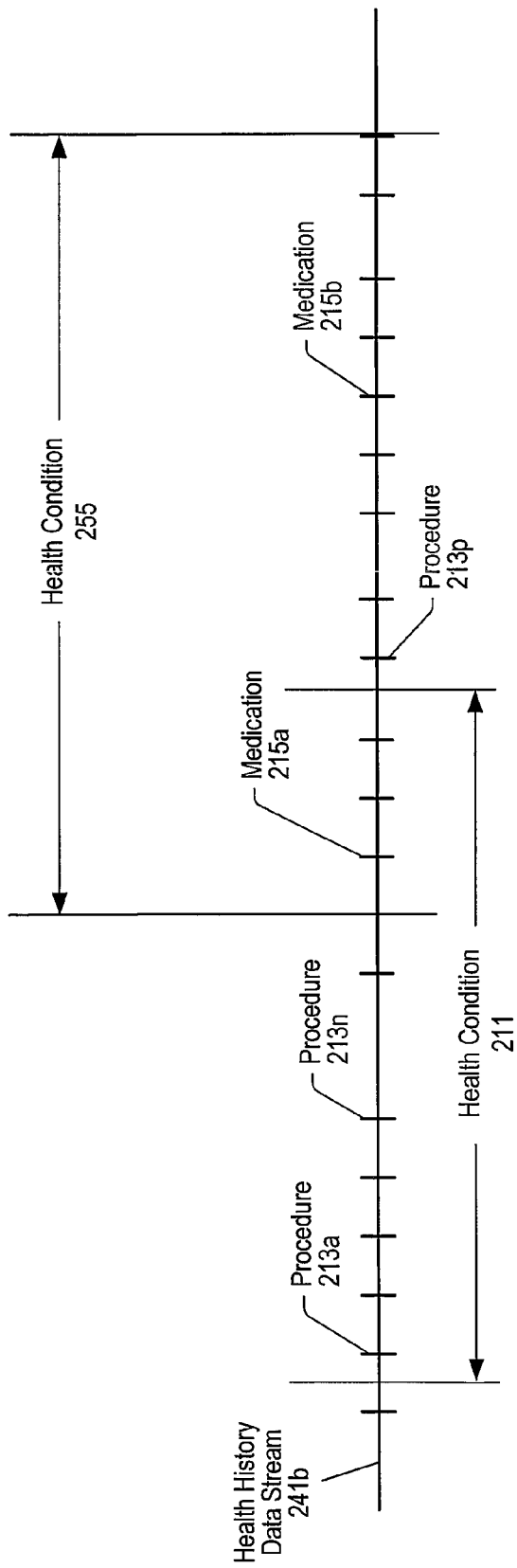

In some embodiments, information for the aggregate healthcare information 150 may be provided to the healthcare information collection and analysis system 130 directly from the healthcare management application 100. In some embodiments, the information for the aggregate healthcare information 150 may be extracted from healthcare information 120 maintained for system users 201 of the healthcare management application 100. In some embodiments, the information may be extracted from healthcare-related information 112 (e.g., in the form of a health history data stream 241 for a healthcare consumer 202) provided to the healthcare management application 100. For example, information may be extracted (e.g., by one or more web services, Extract, Transform, Load (ETL) data warehouse programs, etc.) from the health history data stream 241a,b (e.g., see FIGS. 1c-d) for a healthcare consumer 202 by using a template (or other analytics) or by searching for identifiers within the information (e.g., within the data stream 241a,b) that indicate the presence of relevant information. Health conditions (e.g., health condition 211) may comprise a set of associated procedures 213 and medications 215 that are linked, for example, by a time period for the health condition (e.g., from initial diagnosis to recovery). In some embodiments, health conditions (e.g., health conditions 211 and 255 as seen in FIG. 1d) may overlap. In these embodiments, templates (or other analytics) may be used to separate the procedures 213 and medications 215 associated with each respective health condition. In some embodiments, overlapping procedures, medications, etc. (e.g., medication 215a on health history data stream 241b) may be associated with multiple health conditions (e.g., health condition 211 and health condition 255).

In some embodiments, procedure codes following (and/or associated with) a diagnosed health condition 211 (e.g., as evidenced by diagnostic codes on the timeline) may be extracted and stored in the aggregate healthcare information 150 with other collected information associated with similar diagnostic or procedure codes. In some embodiments, the system may search for procedure codes, medication types, tests, doctor visits, etc. within a time period associated with a specific health condition 211. Time periods associated with specific health conditions 211 may be determined, for example, by examining diagnostic codes in the health history data stream 241. Other specific information about the procedures 213 may also be collected from the information. For example, medications 215 taken by the healthcare consumers 202, procedure and medication costs, amount of costs covered by the healthcare consumers' health plan, their healthcare providers 203, zip codes of the healthcare consumers 202, zip codes of their healthcare providers 203, negotiated procedure costs (for procedure costs that were negotiated), procedure dates, time range (e.g., of healing), etc. may be collected from the information. In some embodiments, only settled costs may be collected (e.g., pending costs may not be used because they may change). In some embodiments, healthcare consumers 202 may be asked specific questions by the system to determine additional information to add to the collected information (e.g., healthcare consumers 202 may be asked to give a quality rating for a specific healthcare provider 203). The information for several healthcare consumers 202 may be aggregated with other information from the healthcare consumers 202 into the aggregate healthcare information 150. The aggregate healthcare information 150 may be accessible to the healthcare information collection and analysis system 130.

In some embodiments, system users 201 of the healthcare management application 100 may agree to waivers of confidentiality with respect to specific information they provide to the system (or information related to them that is provided to the system from other sources). The aggregate healthcare information 150 may also be anomalously mined from information provided by/for the system users 201.

At 252, the aggregate healthcare information 150 may be organized. For example, the aggregate healthcare information 150 may be organized by health condition 211, procedure 213, healthcare provider 203, medication 215, and/or health plan, etc. Other ways of organizing the aggregate healthcare information 150 are also contemplated. The aggregate healthcare information 150 may be organized, for example, to allow system user access of the aggregate healthcare information 150 in a comparative fashion. For example, the aggregate healthcare information 150 may be organized to allow a system user 201 to compare healthcare information related to a specific health condition 211, procedure 213, medication 215, etc. for two or more sources (e.g., two or more healthcare consumers 202). In addition, the healthcare information collection and analysis system 130 may organize the aggregate healthcare information 150 according to criteria such as the gender, age, or zip code of the healthcare consumer 202 along with a zip code of the healthcare provider 203, health plan type, etc. The aggregate healthcare information 150 may also be organized to facilitate system user searches for specific information (e.g., information associated with a specific health condition).

Organizing the aggregate healthcare information 150 may include analyzing the aggregate healthcare information 150. In some embodiments, the healthcare information collection and analysis system 130 may analyze the aggregate healthcare information 150 to determine, for example, the types of procedures 213 and/or medications 215 experienced for a given health condition 211, the average cost of the procedures 213 and/or medications 215, range of costs for procedures 213 and/or medications 215, etc. The system may determine various statistics for the information (e.g., collected costs for the procedures 213, medications 215, etc. may be analyzed to determine, for example, a minimum/maximum cost and/or a top 25%/bottom 25% cost range). Other statistics are also contemplated.

Figure 3:
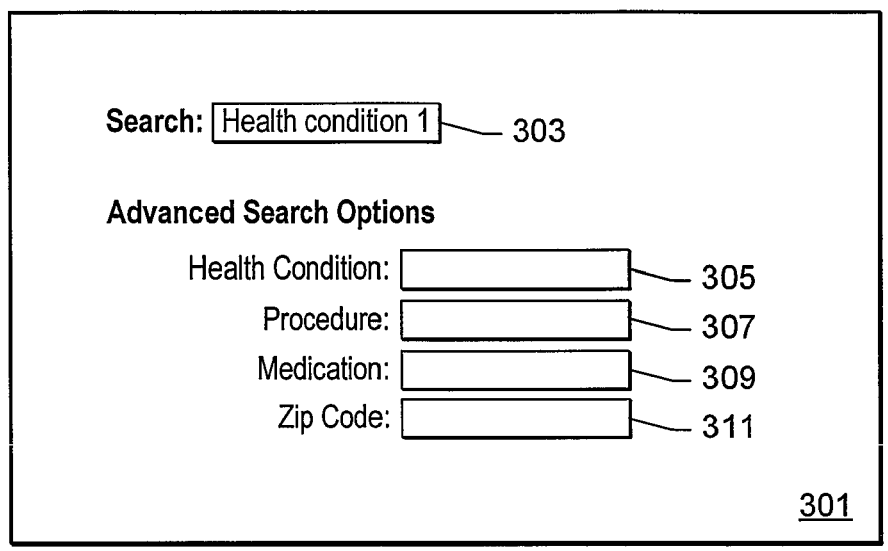
FIG. 3 illustrates a system user interface for searching collected information, according to an embodiment.

At 254, a system user search request may be received. For example, as seen in FIG. 3, the system user 201 may enter a general search term 303 or provide specific search criteria (e.g., health condition 305, procedure 307, medication 309, and/or zip code 311) to further narrow the search. Other search options are also contemplated (e.g., system users 201 may search by specific symptoms). In some embodiments, several fields may be populated to narrow the search (e.g., Health condition="Heart Failure" and Zip Code="99999"). System users 201 may use the search engine interface 301, for example, to find information about a specific health condition 211, procedure 213, medication 215, etc.

At 256, information relative to the system user search request may be presented to the system user 201. In some embodiments, the aggregate healthcare information 150 may be organized into a format specific to the system user's search request. For example, FIG. 4 illustrates a results screen 401 for displaying the results of a search, according to an embodiment. In some embodiments, results for a health condition 211 may include a primary name 403 for the health condition 211 (alternative names may also be displayed), diagnosis procedures 405, treatment medications 407, and treatment procedures 409. Other information may also be provided in the results. For example, in some embodiments, symptom information may be provided with the results (e.g., based on symptoms associated with specific health conditions 211). In addition, in some embodiments, a percentage of healthcare consumers 202 experiencing specific procedures 213 or medications 215 may be provided. In some embodiments, distributions of sub-procedures for a specific health condition 211 may be provided. Additional information may also be returned. For example, test procedures experienced with the health condition, a number of days of physical therapy needed after a specific procedure, a time to heal, etc.

In some embodiments, several results may be returned. For example, specific healthcare consumers 202 (e.g., listed with general descriptors instead of using real names) may also be listed 411 as part of the results 401. A specific healthcare consumer 202 may be selected from the list 411 and another result screen 601 may be provided with the specific healthcare consumer's experience with the health condition 211 (e.g., see FIG. 6). Other results for the health condition may also be returned (e.g., health conditions with similar names).

In some embodiments, selecting a specific procedure 213 or medication 215 (e.g., by clicking on it with a display cursor) or doing a search on the specific procedure 213 or medication 215 may provide a result screen 501 (see FIG. 5) for the specific procedure 213 or medication 215. Specific information for a procedure 213 may be displayed. Information may include the health condition 503, healthcare provider 505 (including healthcare provider name and firm), health plan 507 (including plan type and insurance company), healthcare provider zip code 509, healthcare consumer zip code 511, procedure date and time 513, quality rating 515, medications 517 (e.g., prescribed medications), medication costs 519, etc. Other information may also be provided. In some embodiments, the system may return several search results (e.g., corresponding to several healthcare consumers 202 who have had the specific procedure 213). The system user 201 may review one or more of the search results to view information for other healthcare consumers 202 who have had the same (or similar) procedure 213.

FIG. 6 illustrates a health history associated with a specific healthcare consumer 202 having a specific health condition 211, according to an embodiment. In some embodiments, if the system user 201 selects, for example, "User 4 (Zip Code 99998)" on screen 401 (FIG. 4), screen 601 may be displayed with the health history associated with the specific healthcare consumer 202 (i.e., "User 4"). For example, as seen in result screen 601, the healthcare consumer's health condition 603, the actual diagnosis procedures 605 experienced by the healthcare consumer 202 associated with this health condition 211, the actual treatment medication 607 prescribed to the healthcare consumer 202, and the actual treatment procedure 609 experienced by the healthcare consumer 202 are shown. In some embodiments, if a system user 201 selects a specific procedure 213 or medication 215 (e.g., if the system user 201 clicks on "Procedure 1: Surgical Myectomy") the system user 201 may be presented with a result screen (e.g., result screen 501 in FIG. 5) with the specific information for that healthcare consumer 202 and that procedure 213.

FIG. 7 illustrates a result screen 701 with summary information presented for multiple procedures 213 and medications 215 experienced by the healthcare consumer 202 associated with the health condition 211. For example, for each procedure (e.g., procedure 705) and medication (e.g., medication 707), a healthcare provider 711, procedure initial cost 713, health plan approved cost 715, and amount 717 assigned to the healthcare consumer 202 may be provided. In some embodiments, the information may be provided in other ways (e.g., the information may appear in a pop-up window as a system user rolls a display cursor over a specific procedure 705 or medication 707). Other ways of displaying the additional information are also contemplated. For example, information about a specific healthcare provider 203 may be displayed when a system user "clicks" on the healthcare provider's name in a results screen. The aggregate health information 150 may also be presented to the system user 201 in other ways (e.g., using other result screen formats, etc.)

In some embodiments, the aggregate health information 150 may include statistics such as a number of a specific procedures performed, average cost for insured healthcare consumers 202, average cost for un-insured healthcare consumers 202, and links to information about specific procedures 213 performed by specific healthcare providers 203. The aggregate health information 150 may be used by the system user 201, for example, to determine which healthcare providers 203 have a high degree of experience working with individuals with similar health conditions 211. The information may also be used to determine actual costs paid by other healthcare consumers 202 (which may be used, for example, to help the system user 201 negotiate a lower cost). Other uses of the aggregate health information 150 are also contemplated. Other search interfaces for the aggregate health information 150 are also contemplated.

Figure 8A:
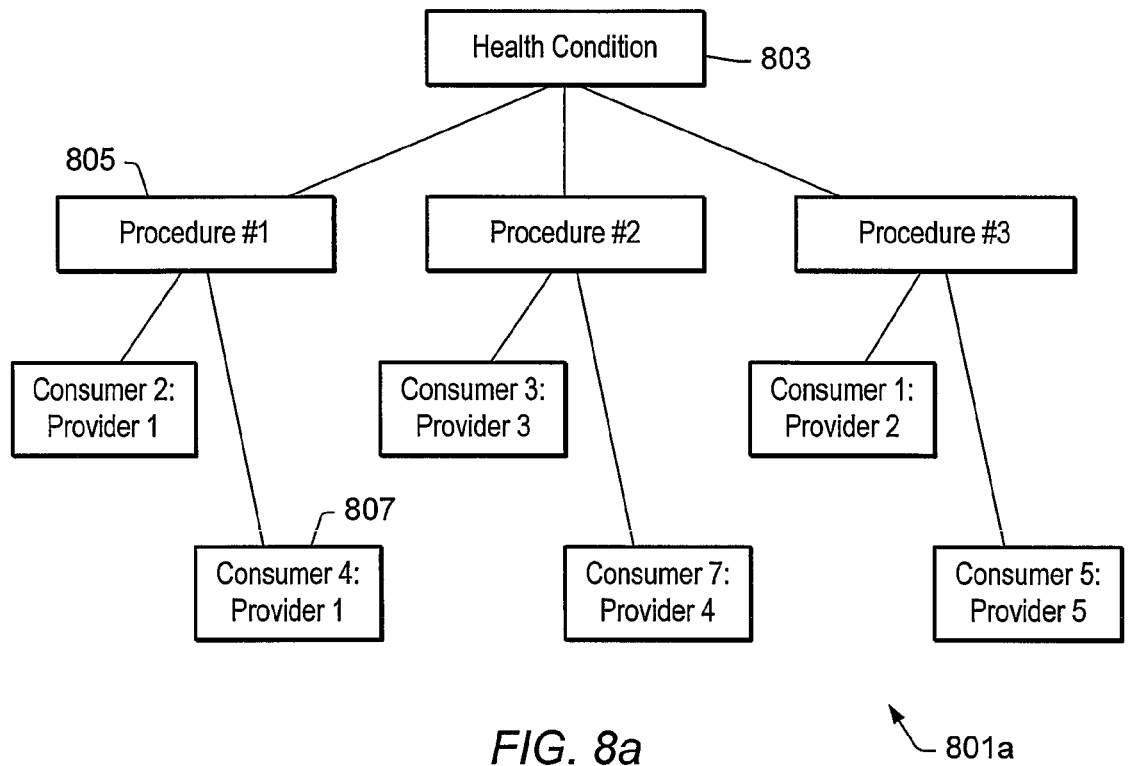
FIGS. 8a-d illustrate various embodiments of an interactive search tree.
Figure 8B:
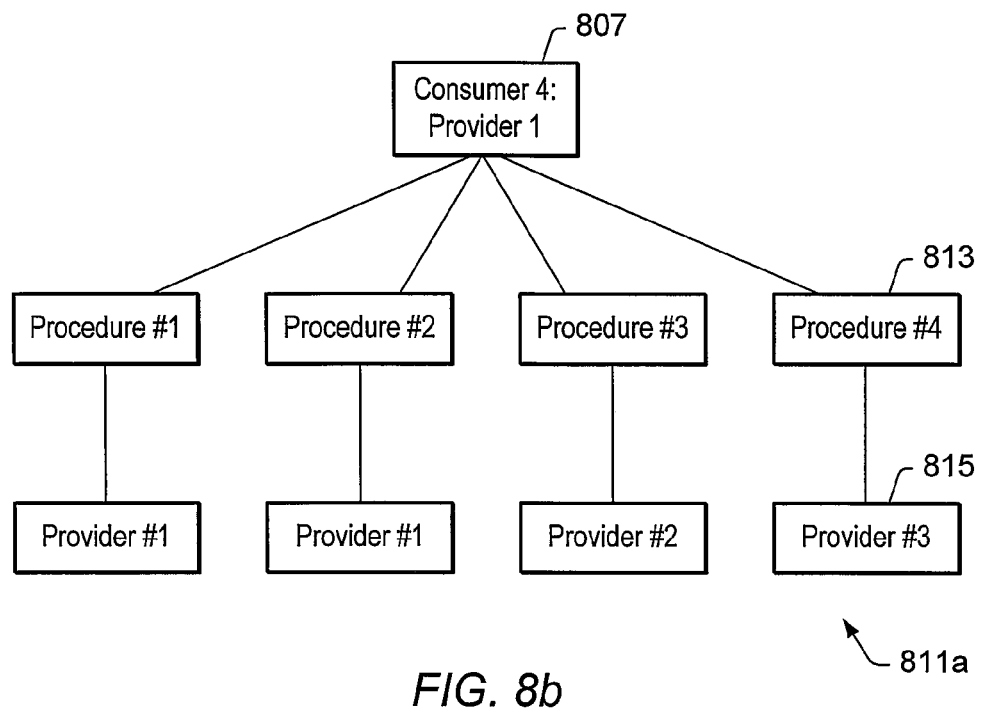
Figure 8C:
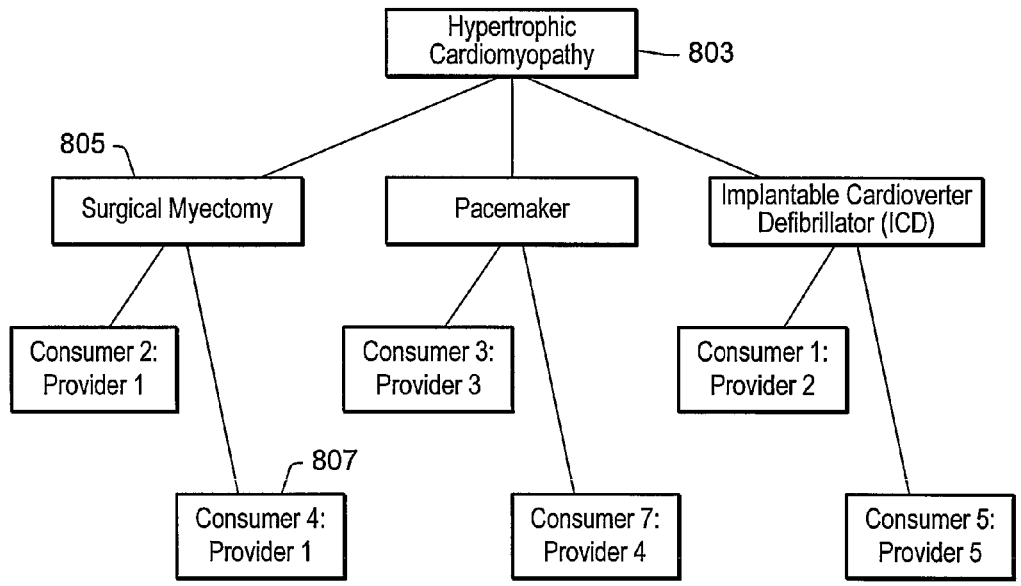
Figure 8D:
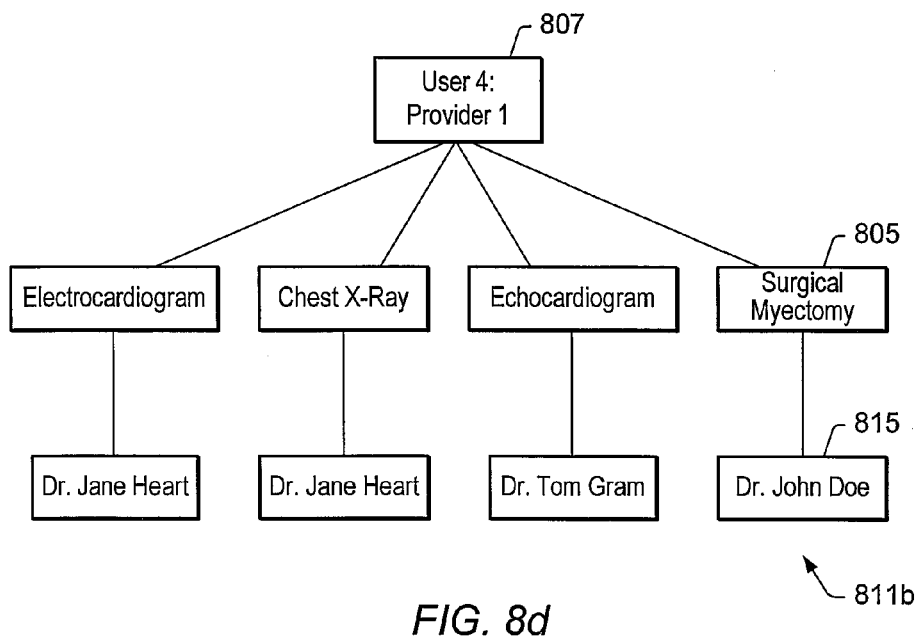

For example, FIGS. 8a-d illustrate interactive tree search interfaces, according to an embodiment. The interactive tree search may display various levels of a search at once to allow the system user 201 to directly select a level they are interested in. For example, as seen in FIG. 8a with tree 801a, the system user 201 may select a specific health condition 211 (e.g., represented by "Health condition" 803), a specific procedure 213 (e.g., represented by "Procedure #1" 805), or a specific healthcare consumer 202 and/or healthcare provider 203 (e.g., represented by "Consumer 4: Provider 1" 807). Other tree level types are also contemplated. For example, various levels of the tree may include specific healthcare providers 203, health plans, medications 215, cost ranges, geographic regions (e.g., by state, city, zip code), etc. In some embodiments, the system user 201 may select a specific tree element by moving a display cursor over the element and clicking on it (e.g., using a computer mouse). Other ways of selecting a tree element are also contemplated (e.g., moving a highlighter box using arrow keys). Selecting a tree element may result in another tree being displayed. For example, selecting "Consumer 4: Provider 1" 807 may result in tree 811a shown in FIG. 8b to be displayed with additional elements (e.g., elements for specific procedures 213 experienced by the selected healthcare consumer 202 (such as represented by "Procedure #4" 813) or a specific healthcare provider 203 that performed the procedure 213 (such as represented by "Provider #3" 815)). Other elements may also be represented in tree 811. Trees 801b and 811b (FIGS. 8c and 8d, respectively) illustrate examples of trees 801a and 811a.

In some embodiments, when a system user 201 selects a tree element, a results screen may be displayed. For example, if the system user 201 selects element 805, display 501 (see FIG. 5) may be displayed showing more information about this element. Other displays are also contemplated.

FIGS. 9a-d illustrate an embodiment of an interactive search inquiry. In some embodiments, the healthcare information collection and analysis system 130 may present the system user 201 with an interactive search inquiry interface 901 including one or more questions 911. In some embodiments, the healthcare information collection and analysis system 130 may present one or more questions 911 to use in determining search criteria. In some embodiments, the system user 201 may be presented with a simple question interface. In some embodiments, an interface 901 may be presented that may include references (e.g., tab 903) to allow the system user 201 to proceed back and forth through the questions 911. For example, tab 905 is highlighted to show the system user 201 what section of the questions 911 the system user 201 is currently in. Subtopics (e.g., subtopic 907) may also be presented to aid navigation through the questions 911. The system user 201 may indicate answers to the questions 911, for example, by clicking answers such as "Yes" or "No" with the display cursor. Other interface options are also contemplated. For example, system users 201 may enter textual information into text fields (e.g., text field 915 in FIG. 9b and text field 917 in FIG. 9d).

As shown in FIG. 9a, the system user 201 may be asked if they know the name of the health condition 211 they are interested in. If so, at 915 in FIG. 9b, the system user 201 may enter the name of the health condition 211. In some embodiments, the system user 201 may also search according to symptoms, procedures 213, medications 215, etc. The system user 201 may also skip "Health conditions" 905, for example, and proceed directly to "Procedures" 903. As seen in FIG. 9c-d, the healthcare information collection and analysis system 130 may allow the system user 201 to search by procedure 213 and enter the procedure name in a text field 917.

In some embodiments, the healthcare information collection and analysis system 130 may present multiple choices for the system user 201 to select from. For example, if the system user 201 enters several symptoms, a list of possible health conditions 211 may be presented to the system user 201 to select from. Other search interfaces 901 and search interface options are also contemplated.

FIGS. 1a-b illustrates the preparation of healthcare management information using a healthcare management application 100 according to one embodiment. The system user 201 may access or execute healthcare management application 100 to manage healthcare information 120 for the system user 201. Healthcare management application 100 may be configured to guide the system user 201 through the healthcare management application 100 step-by-step, and may automatically perform necessary healthcare management in accordance with information input, forms, tables, and formulas stored with or coded into the program. In some embodiments, the healthcare information 120 may be maintained for two or more system users 201 (e.g., a family). The healthcare information 120 may be current healthcare information being accessed for monitoring healthcare billing, insurance payments/deductibles, etc.

Figure 10:
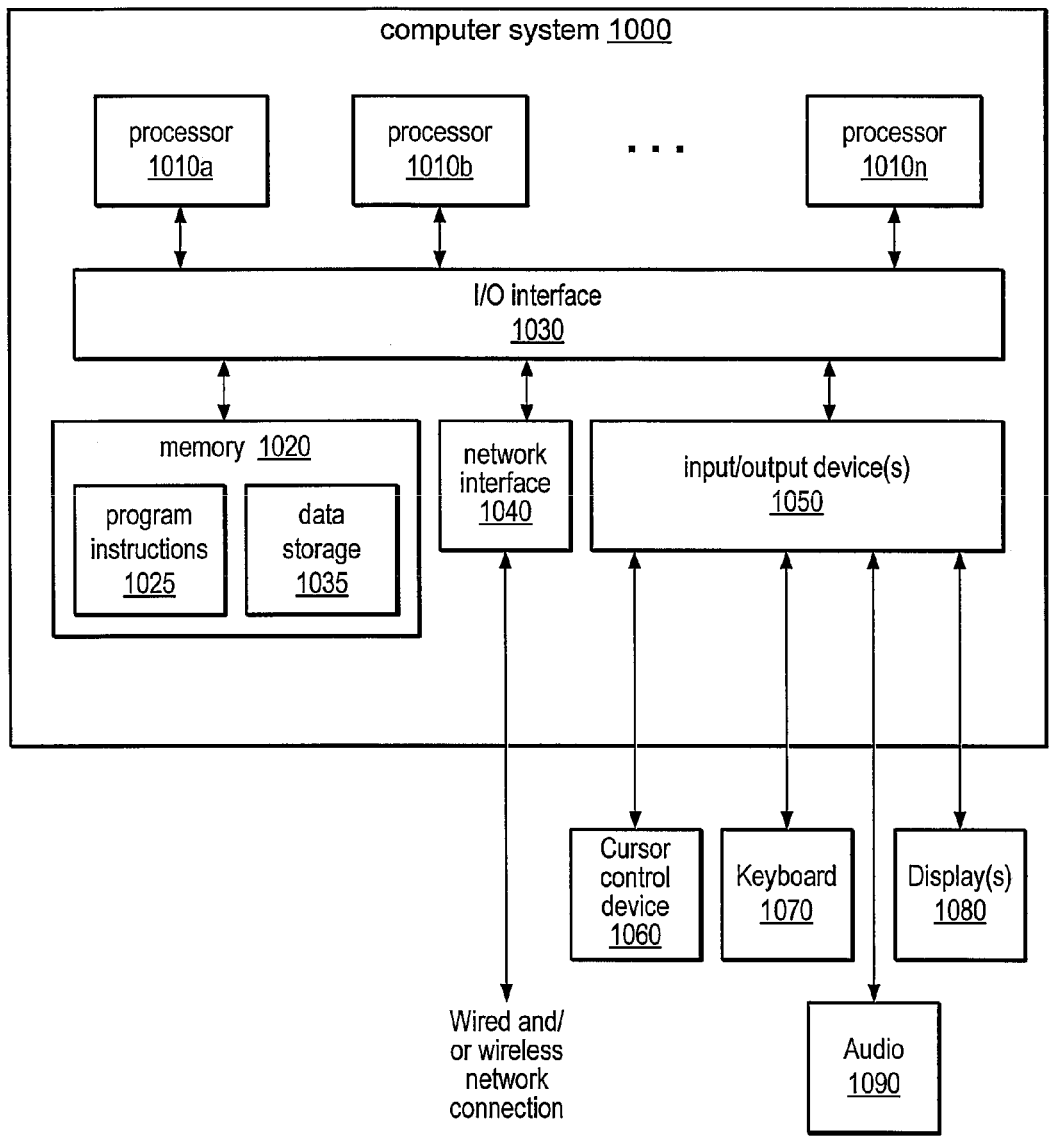
FIG. 10 illustrates a system for implementing the healthcare information collection and analysis system, according to an embodiment.

In some embodiments, an instance of healthcare management application 100 may be installed and executed on a computer system. The computer system may be, but is not limited to, a personal computer (PC) such as a desktop computer, laptop, notebook computer, mobile phone, TV set-top boxes, PDA, or other computing device. An exemplary computer system on which an instance of healthcare management application 100 may be implemented is illustrated in FIG. 10. Alternatively, healthcare management application 100 may be a network- or web-based healthcare management information program which a system user 201 may access (e.g., via a web browser or other application on the system user's local computer system) to prepare various healthcare information forms via a network connection to a remote computer system (e.g., a server), without necessarily installing a healthcare management application 100 on the local computer system.

Healthcare management application 100 may provide a system user 201 interface to guide or step the system user 201 in the preparation and storage of healthcare information 120. Different areas for preparing healthcare management information for different healthcare facilities may be identified as different modules in the healthcare management application 100. Healthcare management information may be associated with a particular module (e.g., recently received health bills, insurance payouts, insurance premiums, etc.) in the healthcare management application 100. Thus, healthcare management application 100 may provide a system user interface that allows the system user 201 to select an appropriate module from among two or more modules for preparing healthcare information 120 for filing with a particular healthcare facility.

Note that the healthcare facility may be a person (e.g., a physician), a business (e.g., a hospital), or other entity for which healthcare information is to be prepared and/or stored.

The healthcare management application 100 may include healthcare documents—e.g., forms, bills, insurance reports, etc. included in the stored healthcare information 120. In some implementations, these healthcare documents may be graphically presented by the healthcare management application 100 to the system user 201 on a display device (e.g., a computer monitor or screen of a hand-held device such as a PDA). In some embodiments, the healthcare management application 100 may provide a information entry mechanism 102 via a system user interface with various system user interface elements (menus, dialog boxes, etc.) and system user-selectable interface items (menu items, buttons, controls, text entry boxes, etc.) whereby the system user 201 may access the documents as needed and enter or modify information on the various healthcare documents using one or more information entry/cursor control mechanisms, such as a keyboard and mouse. These documents may be presented on the system user interface as templates that, when partially or completely filled out, may be "saved" for the particular healthcare facility for which the documents are prepared.

In addition, information from previous and/or related healthcare information and/or from other sources or documents may be transferred 106 into or used in the calculation 104 of values for fields of the electronic healthcare documents. Further, values from a field or fields on one or more electronic healthcare documents may be transferred 106 to other electronic healthcare documents. For example, a calculated value from a bill may be transferred into or used in the calculation of a field (e.g., a required payment) on another electronic healthcare document.

Instead of or as an alternative to entering the necessary information directly to the electronic healthcare documents, some implementations of healthcare management application 100 may provide an input mechanism whereby the system user 201 inputs necessary information into input fields on information entry displays presented to the system user 201 by healthcare management application 100 as electronic healthcare documents. Note that information and/or information from other sources, which may include information and/or information from a previous healthcare management information, from other information entry displays, or from other electronic healthcare documents related to the preparation of the healthcare information 120 under preparation, may be transferred into or used in the calculation of values for some fields in the information entry displays. Information from the information entry displays may then be automatically transferred into the appropriate locations on electronic healthcare management information documents and/or onto other information entry displays. The healthcare management application 100 may perform any necessary calculations using the information from the information entry displays, and possibly information from other sources such as previous healthcare management information, to generate appropriate calculated values for certain fields of the healthcare management information documents.

In addition to user-entered or transferred values, healthcare management application 100 may perform various calculations 104 to generate values for some fields in electronic healthcare documents. Note that inputs to a particular calculation to generate a value for a field may include one or more values from one or more sources. One or more information values entered by the system user 201 via the information entry system user interface may be used in calculations to generate new values from some fields in electronic healthcare documents. In some cases, one or more values from previous healthcare management information may be used in calculations 104 to generate new values for some fields. Calculated values or values from fields on electronic healthcare documents may be used as input into other calculations. Also note that some values used in calculations may be coded as "constants" into the healthcare management application 100, or alternatively may be read into the healthcare management application 100 from a stored information file as needed.

In some embodiments, the system user 201 may enter necessary information via the system user 201 interface of the healthcare management application 100, and, when done, access the system user 201 interface to direct the healthcare management application 100 to complete the healthcare management information 120 under preparation. The healthcare management application 100 may perform any necessary calculations using the entered information and in accordance with healthcare information formulas relevant to the particular healthcare management information 120 under preparation, and possibly information from other sources such as previous healthcare management information or other healthcare-related documents, to generate appropriate calculated values for certain fields of the healthcare information 120 under preparation.

Note that instances of healthcare management application 100 may be installed and executed on many computer systems and used by many system users 201 to prepare various healthcare documents and manage healthcare information. Alternatively, healthcare management application 100 may be a network- or web-based healthcare management information preparation program which many system users 201 may access (e.g., via web browsers or other applications on the system users' local computer systems) to prepare various healthcare information forms via network connections to one or more remote computer systems (e.g., servers), without necessarily installing a healthcare management application 100 on the local computer systems.

While embodiments of the healthcare information collection and analysis system 130 is generally described herein in reference to healthcare management software programs, embodiments of the healthcare information collection and analysis system 130 may be implemented for other types of computer-implemented processes, programs, and applications (which may be collectively identified as computer applications), including but not limited to financial software programs (e.g., tax preparation programs, payroll programs, etc.). Thus, healthcare management application 100 is used as an example herein, and it is to be understood that the Figures and discussions using the healthcare management application 100 as an example are intended to apply to other types of software programs, including financial software programs.

Various components of embodiments of a healthcare information collection and analysis system 130 as described herein may be executed on one or more computer systems, which may interact with various other devices. One such computer system is illustrated by FIG. 10. In the illustrated embodiment, computer system 1000 includes one or more processors 1010 coupled to a system memory 1020 via an input/output (I/O) interface 1030. Computer system 1000 further includes a network interface 1040 coupled to I/O interface 1030, and one or more input/output devices 1050, such as cursor control device 1060, keyboard 1070, audio device 1090, and display(s) 1080. In some embodiments, it is contemplated that embodiments may be implemented using a single instance of computer system 1000, while in other embodiments multiple such systems, or multiple nodes making up computer system 1000, may be configured to host different portions or instances of embodiments. For example, in one embodiment some elements may be implemented via one or more nodes of computer system 1000 that are distinct from those nodes implementing other elements.

In various embodiments, computer system 1000 may be a uniprocessor system including one processor 1010, or a multiprocessor system including several processors 1010 (e.g., two, four, eight, or another suitable number). Processors 1010 may be any suitable processor capable of executing instructions. For example, in various embodiments, processors 1010 may be general-purpose or embedded processors implementing any of a variety of instruction set architectures (ISAs), such as the x86, PowerPC, SPARC, or MIPS ISAs, or any other suitable ISA. In multiprocessor systems, each of processors 1010 may commonly, but not necessarily, implement the same ISA.

System memory 1020 may be configured to store program instructions and/or information accessible by processor 1010. In various embodiments, system memory 1020 may be implemented using any suitable memory technology, such as static random access memory (SRAM), synchronous dynamic RAM (SDRAM), nonvolatile/Flash-type memory, or any other type of memory. In the illustrated embodiment, program instructions and information implementing desired functions, such as those described above for the healthcare information collection and analysis system 130, are shown stored within system memory 1020 as program instructions 1025 and information storage 1035, respectively. In other embodiments, program instructions and/or information may be received, sent or stored upon different types of computer-accessible media or on similar media separate from system memory 1020 or computer system 1000. Generally speaking, a computer-accessible medium may include storage media or memory media such as magnetic or optical media, e.g., disk or CD/DVD-ROM coupled to computer system 1000 via I/O interface 1030. Program instructions and information stored via a computer-accessible medium may be transmitted by transmission media or signals such as electrical, electromagnetic, or digital signals, which may be conveyed via a communication medium such as a network and/or a wireless link, such as may be implemented via network interface 1040.

In one embodiment, I/O interface 1030 may be configured to coordinate I/O traffic between processor 1010, system memory 1020, and any peripheral devices in the device, including network interface 1040 or other peripheral interfaces, such as input/output devices 1050. In some embodiments, I/O interface 1030 may perform any necessary protocol, timing or other information transformations to convert information signals from one component (e.g., system memory 1020) into a format suitable for use by another component (e.g., processor 1010). In some embodiments, I/O interface 1030 may include support for devices attached through various types of peripheral buses, such as a variant of the Peripheral Component Interconnect (PCI) bus standard or the Universal Serial Bus (USB) standard, for example. In some embodiments, the function of I/O interface 1030 may be split into two or more separate components, such as a north bridge and a south bridge, for example. In addition, in some embodiments some or all of the functionality of I/O interface 1030, such as an interface to system memory 1020, may be incorporated directly into processor 1010.

Network interface 1040 may be configured to allow information to be exchanged between computer system 1000 and other devices attached to a network, such as other computer systems, or between nodes of computer system 1000. In various embodiments, network interface 1040 may support communication via wired or wireless general information networks, such as any suitable type of Ethernet network, for example; via telecommunications/telephony networks such as analog voice networks or digital fiber communications networks; via storage area networks such as Fibre Channel SANs, or via any other suitable type of network and/or protocol.

Input/output devices 1050 may, in some embodiments, include one or more display terminals, keyboards, keypads, touchpads, scanning devices, voice or optical recognition devices, or any other devices suitable for entering or retrieving information by one or more computer system 1000. Multiple input/output devices 1050 may be present in computer system 1000 or may be distributed on various nodes of computer system 1000. In some embodiments, similar input/output devices may be separate from computer system 1000 and may interact with one or more nodes of computer system 1000 through a wired or wireless connection, such as over network interface 1040.

As shown in FIG. 10, memory 1020 may include program instructions 1025, configured to implement at least a portion of embodiments of the healthcare information collection and analysis system 130 as described herein, and information storage 1035, comprising various documents, tables, databases, etc. accessible by program instructions 1025. In one embodiment, program instructions 1025 may include software elements of the healthcare information collection and analysis system 130 illustrated in the Figures, and information storage 1035 may include information used in embodiments of the healthcare information collection and analysis system 130. In other embodiments, different software elements and information may be included.

Those skilled in the art will appreciate that computer system 1000 is merely illustrative and is not intended to limit the scope of the healthcare information collection and analysis system 130 as described herein. In particular, the computer system and devices may include any combination of hardware or software that can perform the indicated functions, including computers, network devices, internet appliances, PDAs, wireless phones, pagers, etc. Computer system 1000 may also be connected to other devices that are not illustrated, or instead may operate as a stand-alone system. In addition, the functionality provided by the illustrated components may in some embodiments be combined in fewer components or distributed in additional components. Similarly, in some embodiments, the functionality of some of the illustrated components may not be provided and/or other additional functionality may be available.

Those skilled in the art will also appreciate that, while various items are illustrated as being stored in memory or on storage while being used, these items or portions of them may be transferred between memory and other storage devices for purposes of memory management and information integrity. Alternatively, in other embodiments some or all of the software components may execute in memory on another device and communicate with the illustrated computer system via inter-computer communication. Some or all of the system components or information structures may also be stored (e.g., as instructions or structured information) on a computer-accessible medium or a portable article to be read by an appropriate drive, various examples of which are described above. In some embodiments, instructions stored on a computer-accessible medium separate from computer system 1000 may be transmitted to computer system 1000 via transmission media or signals such as electrical, electromagnetic, or digital signals, conveyed via a communication medium such as a network and/or a wireless link. Various embodiments may further include receiving, sending or storing instructions and/or information implemented in accordance with the foregoing description upon a computer-accessible medium. Accordingly, the present invention may be practiced with other computer system configurations.

Various embodiments may further include receiving, sending or storing instructions and/or information implemented in accordance with the foregoing description upon a computer-accessible medium. Generally speaking, a computer-accessible medium may include storage media or memory media such as magnetic or optical media, e.g., disk or DVD/CD-ROM, volatile or non-volatile media such as RAM (e.g. SDRAM, DDR, RDRAM, SRAM, etc.), ROM, etc. As well as transmission media or signals such as electrical, electromagnetic, or digital signals, conveyed via a communication medium such as network and/or a wireless link.

The various methods as illustrated in the Figures and described herein represent exemplary embodiments of methods. The methods may be implemented in software, hardware, or a combination thereof. The order of method may be changed, and various elements may be added, reordered, combined, omitted, modified, etc.

Various modifications and changes may be made as would be obvious to a person skilled in the art having the benefit of this disclosure. It is intended that the invention embrace all such modifications and changes and, accordingly, the above description to be regarded in an illustrative rather than a restrictive sense.

What is claimed is:

1. A system, comprising:
one or more processors;
a display device coupled to the one or more processors; and
a memory coupled to the one or more processors, wherein the memory comprises program instructions executable by the one or more processors to implement a network-based service, wherein the network-based service is configured to:
collect, from a plurality of types of sources, healthcare information about health conditions, related procedures, and actual costs, the conditions, procedures, medications and costs having been actually received by and thus experienced by a first set of healthcare consumers, wherein the healthcare information comprises a quality rating relating to the consumer assessment of the quality of a procedure that consumer has experienced, further wherein the types of sources comprise a healthcare consumer source and at least one of either a health plan provider source or a healthcare provider source, wherein a healthcare consumer is a patient who received a healthcare procedure performed by one or more healthcare providers, and further wherein a healthcare provider is an individual who performed at least a portion of the procedure received by a patient;
analyze the collected healthcare information to determine one or more of types of procedures or medications experienced for a given health condition, average cost of one or more procedures or medications, and a range of costs for procedures or medications;
organize the collected healthcare information; and
provide at least a portion of the organized healthcare information to a patient user of the network-based service other than a consumer of the plurality of healthcare consumers in response to a search request by the patient user for determining procedures and medications they can expect with certain health conditions, the search request including a request for information associated with a specified health condition, the provided portion of the organized healthcare information including information for one or more procedures associated with the specified health condition, the provided information for the one or more procedures including a cost of a procedure of the one or more procedures, wherein the cost of the procedure of the one or more procedures is a negotiated cost, the provided portion of the organized healthcare information being provided as a comparison of procedures, medications and actual costs associated with a particular health condition previously experienced by two or more healthcare consumers of the first set of healthcare consumers other than the patient user, the provided portion of the organized healthcare information further including a percentage of healthcare consumers that experienced specific procedures or medications associated with the health condition.

2. The system as recited in claim 1, wherein the plurality of types of sources include a plurality of consumer users of the network based service who use a healthcare management application of the network-based service to enter their respective healthcare information, and wherein the collected healthcare information is at least partially collected from the entered respective healthcare information.

3. The system as recited in claim 1, wherein the search request is submitted from the consumer user of the network-based service through an interactive search interface provided by the network-based service.

4. The system as recited in claim 1, wherein said collecting healthcare information comprises extracting information linked to procedure codes from a health history provided to the network-based service.

5. The system as recited in claim 1, wherein said organizing the collected healthcare information comprises grouping the collected healthcare information according to health conditions.

6. The system as recited in claim 1, wherein the search request includes a request for healthcare information for a specific geographic region.

7. The system as recited in claim 1, wherein the healthcare information comprises an amount billed, an amount allowed by a health plan provider, and an amount the consumer paid.

8. A computer readable storage medium, comprising a nontransitory computer readable storage medium having instructions stored therein which when executed by a processor perform:
collecting, from a plurality of types of sources, healthcare information about health conditions, related procedures, and actual costs, the conditions, procedures, medications and costs having been actually received by and thus experienced by a first set of healthcare consumers, wherein the healthcare information comprises a quality rating relating to the consumer assessment of the quality of a procedure that consumer has experienced, further wherein the types of sources comprise a healthcare consumer source and at least one of either a health plan provider source or a healthcare provider source, wherein a healthcare consumer is a patient who received a healthcare procedure performed by one or more healthcare providers, and further wherein a healthcare provider is an individual who performed at least a portion of the procedure received by a patient;
analyze the collected healthcare information to determine one or more of types of procedures or medications experienced for a given health condition, average cost of one or more procedures or medications, and a range of costs for procedures or medications;

organizing the collected healthcare information; and providing at least a portion of the organized healthcare information to a patient user of the network-based service other than a consumer of the plurality of healthcare consumers in response to a search request by the patient user for determining procedures and medications they can expect with certain health conditions, the search request including a request for information associated with a specified health condition, the provided portion of the organized healthcare information including information for one or more procedures associated with the specified health condition, the provided information for the one or more procedures including a cost of a procedure of the one or more procedures, wherein the cost of the procedure of the one or more procedures is a negotiated cost, the provided portion of the organized healthcare information being provided as a comparison of procedures, medications and actual costs associated with a particular health condition previously experienced by two or more healthcare consumers of the first set of healthcare consumers other than the patient user, the provided portion of the organized healthcare information further including a percentage of healthcare consumers that experienced specific procedures or medications associated with the health condition.

9. The computer readable storage medium as recited in claim 8, wherein the plurality of types of sources include a plurality of consumer users of the network based service who use a healthcare management application of the network-based service to enter their respective healthcare information, and wherein the collected healthcare information is at least partially collected from the entered respective healthcare information.

10. The computer readable storage medium as recited in claim 8, wherein the search request is submitted from the consumer user of the network-based service through an interactive search interface provided by the network-based service.

11. The computer readable storage medium as recited in claim 8, wherein said collecting healthcare information comprises extracting information linked to procedure codes from a health history provided to the network-based service.

12. The computer readable storage medium as recited in claim 8, wherein said organizing the collected healthcare information comprises grouping the collected healthcare information according to health conditions.

13. The computer readable storage medium as recited in claim 8, wherein the search request includes a request for healthcare information for a specific geographic region.

14. The computer readable storage medium as recited in claim 8, wherein the healthcare information comprises an amount billed, amount paid by the health plan, and an amount the consumer paid.

* * * * *